June 9, 1953 F. MEILLAND Plant Pat. 1,193
ROSE PLANT
Filed June 11, 1952
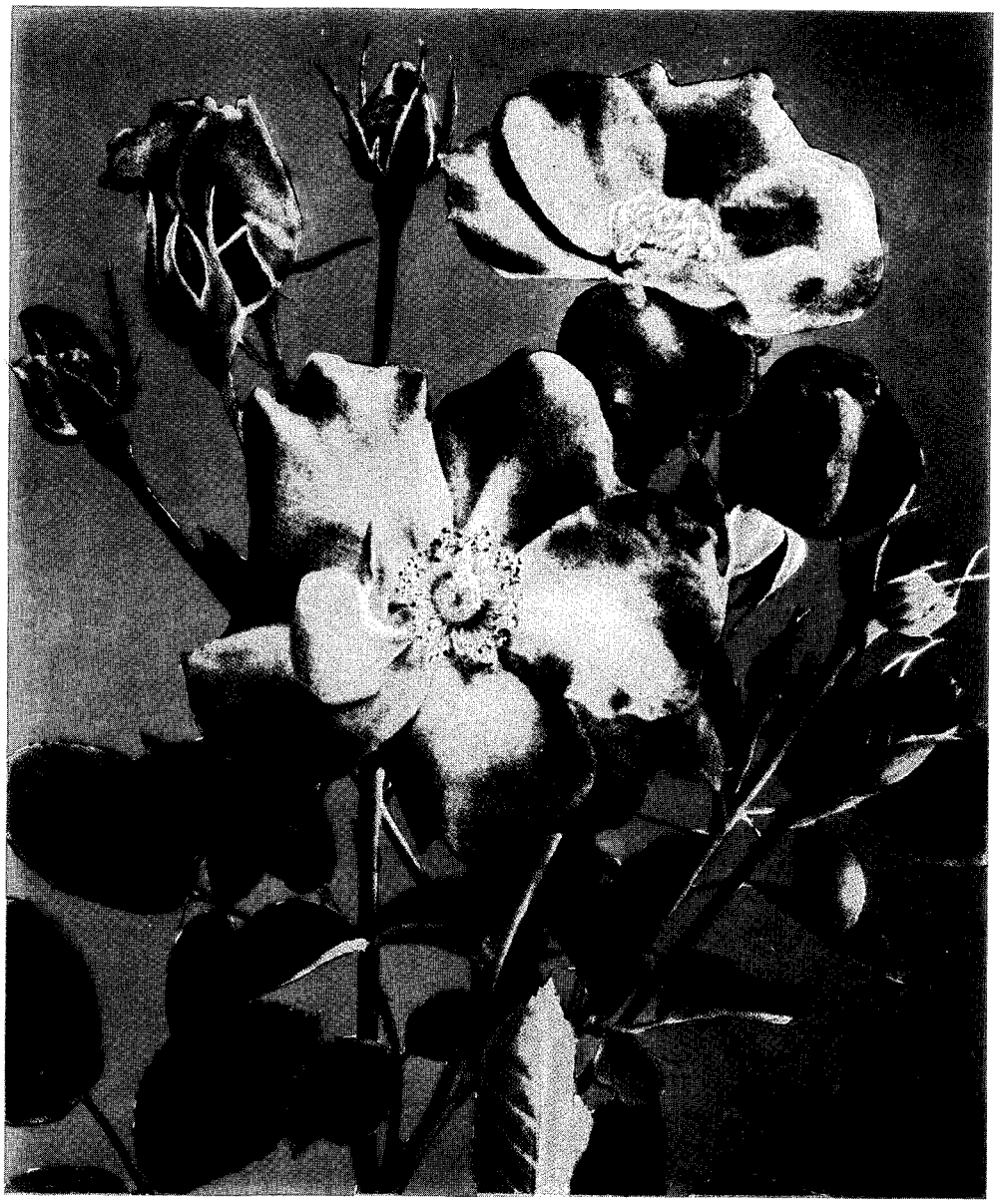
Inventor.
Francis Meilland
By: Robert Cobb
Attorneys.

Patented June 9, 1953

Plant Pat. 1,193

UNITED STATES PATENT OFFICE 1,193

ROSE PLANT

Francis Meilland, Cap Azura, Cap d'Antibes, France, assignor to The Conard-Pyle Company, West Grove, Pa., a corporation of Pennsylvania Application June 11, 1952, Serial No. 293,032
In France September 24, 1951

1 Claim. (Cl. 47—61)

The present invention relates to a new and distinct variety of rose plant of the hybrid polyantha class, originated by me by crossing the variety "Alain" (unpatented) with the variety "Orange Triumph" (unpatented).

The primary objective in making this cross was to produce a new rose variety of the semi-double, large-flowered hybrid polyantha class, with its blooms of a relatively fixed, bright orange-red color, while at the same time retaining the best characteristics of the class in respect to hardiness, vigor, disease resistance and freedom of bloom. This objective was fully achieved, as evidenced by the fact that the new variety does retain the best characteristics of this class, as mentioned above, and at the same time, it bears flowers of a persistent, brilliant, even Spectrum Red coloring previously lacking in other semi-double, large-flowered hybrid polyantha roses. While the color of the blooms does fade eventually by reason of the fact that the blooms are relatively long-lasting, the coloring of the 3-day-old blooms remains substantially the same as that of the newly opened blooms, and no appreciable change in color has been observed even in the case of 5- to 7-day-old blooms.

My new variety is still further characterized and distinguished from its parents, as well as from all other varieties of this class, by the unique combination of the color characteristics aforementioned with the clustered character of the florescence, the semi-double, flattened form of the open blooms, and the comparative uniformity of the color in the buds and blooms of different ages.

Asexual reproduction of my new variety by buddings both at Tassin-les-Lyon, France, and at West Grove, Pennsylvania, U. S. A., shows that the foregoing characteristics and distinctions come true to form and are established and transmitted through succeeding propagations.

The accompanying drawing shows specimens of my new variety, with the flowers and foliage in different stages of development, and with the colors depicted in the drawing as nearly true as it is reasonably possible to make the same in an illustration of this character.

The following is a detailed description of my new variety, with color terminology in accordance with Ridgway's Color Standards and Nomenclature, except where general color terminology of ordinary dictionary significance is obvious:

Type: Hardy; bush; outdoor; seedling; for cut flowers and for garden decoration.

Class: Hybrid polyantha.

Breeding: Seedling.

*Seed parent.*—"Alain."

*Pollen parent.*—"Orange triumph."

Propagation: Holds its distinguishing characteristics through succeeding propagations by budding.

*Flower*

Locality where grown and observed: West Grove, Pennsylvania, U. S. A.

Flowers borne: Several to stem; in irregular rounded cluster; on strong, medium length stems.

Quantity of bloom: Free, outdoors.

Continuity: Continuous.

Fragrance: Fairly strong for a Floribunda; spicy.

Bud:

*Peduncle.*—Medium length; medium heavy; strong; medium green; rough; numerous minute prickles that can be felt but barely seen without magnification.

*Before calyx breaks.*—Size—medium large. Form—long; pointed; with a conspicuous neck; with a few small foliaceous appendages on the surface of the bud; with slender, pointed foliaceous parts extending beyond the tip of the bud equal to ½ or more of its length.

*As calyx breaks.*—Color—Nopal Red, Plate I, with blackish shadings from the apex downward.

*As first petal opens.*—Size—medium large. Form—long; cylindrical. Color: outside—Nopal Red, Plate I, with dark shadings from the apex downward; inside—Scarlet Red, Plate I, at base to Spectrum Red, Plate I, darkening toward the apex almost to Carmine, Plate I, but not quite, as it keeps the basic brilliance of the Spectrum Red beneath the darker shading that appears as a velvety overlay.

*Opening.*—Opens up well.

Bloom:

*Size, when fully open.*—Medium large; 2¾ inches to 3½ inches.

*Petalage.*—Semi-double; from 5 to 9 petals; arranged irregularly.

*Form.*—Cupped at first; soon becoming wide open, almost flat; petals being at first loosely cupped; becoming later before maturity loosely flat, with some of the petal edges loosely curled outward, keeping this form to maturity.

Petals: Medium thick; with inside velvety and outside with crepe-like surface.

*Shape.*—Outer—round, with apex flat; with 1 or 2 notches. Intermediate—rounded, with apex flat or with 1 notch. Inner—rounded, with edges often irregular; apex flat or waved or irregularly notched.

This description of a newly opened flower was made from a rose grown in a greenhouse in the month of March, at West Grove, Pennsylvania, U. S. A.:

*Color.*—Outer petal: outside surface—Spectrum Red, Plate I, at base, shading gradually to Carmine, Plate I, at apex; inside surface—Spectrum Red, Plate I. Outer portions are slightly darker than the Spectrum Red of the color chart, but closer to it than to any other color shown on the chart. Intermediate petal: outside surface—Spectrum Red, Plate I, at base, shading gradually to Carmine, Plate I, at apex; inside surface—Spectrum Red, Plate I. Outer portions are slightly darker than the Spectrum Red of the color chart, but closer to it than to any other color shown on the chart. Inner petal: outside surface—Spectrum Red, Plate I, at base, shading gradually to Carmine, Plate I, at apex; inside surface—Spectrum Red, Plate I. Outer portions are slightly darker than the Spectrum Red of the color chart, but closer to it than to any other color shown on the chart.

This description was made from a rose that was open for three days in a greenhouse in the month of March, at West Grove, Pennsylvania, U. S. A.:

*Color.*—Outer petal: outside surface—Spectrum Red, Plate I, at base, shading gradually to Carmine, Plate I, at apex; inside surface—Spectrum Red, Plate I. Outer portions are slightly darker than the Spectrum Red of the color chart, but closer to it than to any other color shown on the chart. Inner petal: outside surface—Spectrum Red, Plate I, at base, shading gradually to Carmine, Plate I, at apex; inside surface—Spectrum Red, Plate I. Outer portions are slightly darker than the Spectrum Red of the color chart, but closer to it than to any other color shown on the chart.

*General color effect.*—Newly opened flower—Bright Spectrum Red, Plate I. Three days open—Bright Spectrum Red, Plate I.

*Behavior.*—Persist.

*Reproductive organs*

Stamens: Medium number; arranged in circular band about pistils.

*Filaments*: All with anthers; of varying lengths, short, medium and long. Color—yellowish and reddish at first, becoming Mallow Purple or Tyrian Pink, Plate XII, with white base.

Anthers: All open at once; medium large. Color—Cadmium Yellow, Plate III, at first, becoming light yellow with dark brown centers.

Pollen: Abundant. Color—yellow spangling the petals.

Pistils: Medium number.

Styles: Somewhat uneven; medium length; medium weight; bunched.

Stigma: Color—yellow.

Ovaries: All enclosed in calyx.

*Plant*

Foliage:

*Leaves.*—Compound of 3, 5 or 7 leaflets; normal abundance; medium size; moderately heavy; leathery.

*Leaflets.*—Shape—oval, with apex acute. Base—round. Margin—serrate.

*Color.* — Mature: upper surface — Cedar Green, Plate VI; under surface—Chromium Green, Plate XXXII. Young: upper surface—Hellebore Green, Plate XVII, stained with red-brown at first; under surface—Very young leaves Mineral Red, Plate XXVII. Later, mixed with Biscay Green, Plate XVII, the green increasingly predominant with age.

*Rachis.*—Medium weight. Upper side—grooved. Under side—On some, sparsely thorny. Rachis of some leaves, especially upper ones, without thorns.

*Stipules.*—Moderately long; moderately narrow; with medium length points turning out at an angle of less than 90°.

*Disease.*—Resistant to mildew and blackspot, as determined by comparison with other varieties grown under comparable conditions.

Growth:

*Habit.*—Bushy; upright.

*Growth.*—Moderate.

*Canes.*—Medium weight.

*Main stems.*—Color—green. Prickles or thorns—several; short to medium length; practically straight; with medium length narrow base. Hairs—none.

*Branches.*—Color—bright green. Prickles or thorns—several; medium short; practically straight; with narrow base. Hairs—none.

*New shoots.*—Color—bright light green, Prickles or thorns—few; short; straight; with narrow base. Hairs—none.

I claim:

A new and distinct variety of rose plant of the large-flowered hybrid polyantha class, substantially as herein shown and described, characterized particularly as to novelty by the relatively fixed, persistent, brilliant, uniform Spectrum Red coloring of its buds and blooms in their different stages of development, by the semi-double and clustered habit of growth of its blooms, by the relatively flattened form of its open blooms, by the long-lasting quality of its blooms without tendency to fade, and combined with the best characteristics of other varieties of its class in respect to hardiness, vigor, disease resistance and freedom of bloom.

FRANCIS MEILLAND.

No references cited.